(12) United States Patent
Liu

(10) Patent No.: US 12,708,718 B2
(45) Date of Patent: Aug. 18, 2026

(54) DISPOSABLE INJECTION PEN

(71) Applicant: ESC Medtech (Suzhou) Co., Ltd, Suzhou (CN)

(72) Inventor: Kai Liu, Suzhou (CN)

(73) Assignee: ESC Medtech (Suzhou) Co., Ltd, Suzhou City (CN)

( * ) Notice: Subject to any disclaimer, the term of this patent is extended or adjusted under 35 U.S.C. 154(b) by 341 days.

(21) Appl. No.: 18/527,654

(22) Filed: Dec. 4, 2023

(65) Prior Publication Data

US 2024/0108814 A1 Apr. 4, 2024

Related U.S. Application Data

(63) Continuation of application No. PCT/CN2023/104394, filed on Jun. 30, 2023.

(30) Foreign Application Priority Data

Jun. 25, 2023 (CN) ........................ 202310745630.0

(51) Int. Cl.
*A61M 5/32* (2006.01)
*A61M 5/34* (2006.01)

(52) U.S. Cl.
CPC .......... *A61M 5/322* (2013.01); *A61M 5/3202* (2013.01); *A61M 5/34* (2013.01)

(58) Field of Classification Search
CPC ....... A61M 5/322; A61M 5/3202; A61M 5/34
See application file for complete search history.

(56) References Cited

U.S. PATENT DOCUMENTS

2016/0193412 A1* 7/2016 Cereda .................... A61M 5/50 604/125
2020/0324051 A1* 10/2020 Atterbury ........... A61M 5/3271
2022/0040408 A1* 2/2022 Dobson ............... A61M 5/2033

FOREIGN PATENT DOCUMENTS

CN 106999659 A 8/2017
CN 110292683 A 10/2019
CN 112076364 A 12/2020
CN 112843389 A 5/2021
CN 112933346 A 6/2021
CN 213491190 U 6/2021
CN 113117191 A 7/2021
CN 113499513 A 10/2021
WO 2021160540 A1 8/2021

* cited by examiner

*Primary Examiner* — Dung T Ulsh

(57) ABSTRACT

A disposable injection pen includes a pen casing, an injection head mechanism and a trigger mechanism. The injection head mechanism includes a barrel arranged in the pen casing and a needle arranged on a top thereof. The barrel is provided with a rubber plug. The trigger mechanism includes a protective sheath arranged in the pen casing and movably wrapped around the needle. A bottom of the protective sheath movably abuts against a sliding part. An outside of the sliding part is sleeved with a secondary spring whose bottom is fixedly connected to a bottom of the pen casing. An inside of the sliding part is movably clamped with a push rod with an open bottom. An inner top of the push rod is connected to an inner bottom of the sliding part through a primary spring.

8 Claims, 14 Drawing Sheets

DISPOSABLE INJECTION PEN

CROSS-REFERENCE TO RELATED APPLICATIONS

This application is a continuation of International Patent Application No. PCT/CN2023/104394, filed on Jun. 30, 2023, which claims the benefit of priority from Chinese Patent Application No. 202310745630.0, filed on Jun. 25, 2023. The content of the aforementioned application, including any intervening amendments thereto, is incorporated herein by reference in its entirety.

TECHNICAL FIELD

This application relates to medical appliances, and more specifically to a disposable injection pen.

BACKGROUND

Syringe is a commonly used medical appliance. The conventional syringe merely includes three core components, namely, barrel, needle, and piston. By pushing the piston, the drug in the barrel can be conveniently injected into the body through the needle. However, when used in non-medical occasions, such as at home, the operations, such as injection, administration and needle withdrawal, have a certain skill requirement for those non-medical professionals. Moreover, after the injection, the exposed needle is dangerous, and thus needs special disposal. Therefore, the automatic syringe has been created to simplify the injection operation and enhance the safety. By means of the automatic syringe, the continuous injection, infusion and needle withdrawal can be completed with simple operation. As the automatic syringe is designed as a pen in shape for the convenience of storage and holding, it is also known as the injection pen.

At present, a variety of automatic injection pens with the above functions are available commercially, but they still have some shortcomings. For example, the needle insertion is performed by manual pressing, which may make the user feel fearful, leading to a poor user experience.

Therefore, it is necessary to design a new automatic injection pen with a better safety, reliability and user experience.

SUMMARY

An objective of the present disclosure is to provide an automatic injection pen, in which the trigger mechanism can drive the needle tip to automatically and quickly enter the skin for drug injection, relieving the user's pain and fear.

To achieve the above objective, this application provides a disposable injection pen, comprising:

a pen casing;

an injection head mechanism; and a trigger mechanism;

wherein the injection head mechanism comprises a barrel arranged in the pen casing and a needle arranged on a top of the barrel; and a rubber plug is provided in the barrel; and the trigger mechanism comprises a protective sheath arranged in the pen casing, and the protective sheath is configured to movably wrap the needle; a bottom of the protective sheath movably abuts against a sliding part; an outside of the sliding part is sleeved with a secondary spring whose bottom is fixedly connected to a bottom of the pen casing; a push rod with an open bottom is movably clamped inside the sliding part; an inner top of the push rod is connected to an inner bottom of the sliding part through a primary spring; when the protective sheath is pressed, the sliding part moves downward such that the push rod moves upward to push the rubber plug forward; and after an injection is completed, the push rod is detached from an inner cavity of the sliding part, and the sliding part is driven by the primary spring to hit the bottom of the pen casing to produce a sound that indicates completion of the injection.

In some embodiments, the pen casing comprises an upper casing portion and a lower casing portion fixedly clamped with each other; two sides of an inner wall of the lower casing portion are each provided with a protrusion; the protrusion is fixed to an inner wall of the barrel; and two sides of the protective sheath are each provided with an avoidance hole fitting the protrusion.

In some embodiments, the sliding part comprises an outer sliding block and a main body; two sides of the outer sliding block are each provided with a guiding groove, and a guiding plate is fixed longitudinally in the guiding groove; and the main body of the sliding part is configured to slide along the guiding plate to be sleeved into an inner cavity of the outer sliding block.

In some embodiments, two sides of an outer wall of the outer sliding block are each provided with a blocking rib; an upper end of the secondary spring abuts against a lower side of the blocking rib; and the secondary spring abuts against an inner bottom of the lower casing portion.

In some embodiments, the main body of the sliding part comprises a cylinder and two arc-shaped connecting plates respectively connected to two sides of an upper portion of the cylinder; an upper end of each of the two arc-shaped connecting plates is connected to a first elastic hook located at an opening of an upper end of the outer sliding block; and a middle portion of each of the two arc-shaped connecting plates is connected with an arc-shaped insertion plate, wherein two arc-shaped insertion plates each have an opening opposite to each other, and each are fixed to a corresponding guiding plate.

In some embodiments, the push rod is hollow; two sides of an outer bottom of the push rod are each connected with a boss located in the guiding groove; an upper surface of the boss is configured to inclinedly fit a side wall of the arc-shaped connecting plate; and the boss is configured to be slidably inserted into a corresponding arc-shaped insertion plate and to be in contact with the guiding plate during a downward movement of the arc-shaped connecting plate.

In some embodiments, the opening of the upper end of the outer sliding block is connected to a fixing block in movable contact with the boss; an upper surface of the fixing block is in movable contact with a lower surface of the first elastic hook; each of two outer walls of the fixing block has a protruding portion; and two sides of an inner wall of the lower casing portion are each provided with a clamping slot fitting the protruding portion.

In some embodiments, the primary spring is fixedly connected between an inner bottom of the cylinder and an inner top of the push rod.

In some embodiments, a spring-guiding pin is fixedly connected to the inner bottom of the cylinder; and the primary spring is wound around an outside of the spring-guiding pin.

In some embodiments, an upper end of the lower casing portion is in snap-fit connection with a cap member; the cap member comprises a cap head, a second elastic hook and a needle cap; the second elastic hook is connected to two sides of an inner top of the cap head; and the needle cap is in snap-fit connection with the cap head through the second elastic hook, and is configured to movably cover a periphery of the needle.

The present application has at least the following beneficial effects. The needle tip of the trigger mechanism can automatically and quickly enter the skin for drug injection, relieving the pain and fear of the user. The disposable injection pen provided herein is operated as follows. (S1) The pen cap member and elastic hooks B connected to the cap head are removed to pull out the needle cap. (S2a) The protective sheath is pressed to drive the outer sliding block to move downward and compress the secondary spring, and then the arc-shaped connecting plate in the main body will also move downward. In this case, the boss on the side wall at the lower end of the push rod will rotate at a certain angle along the inclined surface that fits with the arc-shaped connecting plate into the inner cavity of the main body through the push force of the main spring, and the push rod pushes the rubber plug to inject the medicinal liquid. (S2b) After the medicinal liquid injection is completed, the push rod disengages from the inner cavity of the main body, and the main body is bounced to the bottom of the upper casing portion by the primary spring and subjected to impact to produce an end sound indicating the completion of the medicinal liquid injection. (S3) After the medicinal liquid injection is completed, the injection pen is removed. At this time, the pre-compressed secondary spring pushes the outer sliding block and the protective sheath to move forward. When the outer sliding block returns to the original position, the two elastic hooks A at the upper end of the main body are respectively clamped into the two square holes in the side wall at the upper end of the outer sliding block. The protective sheath is pressed again, and the protective case is prevented from moving due to the support of the elastic hooks A of the main body for the outer sliding block, forming an anti-needling function.

Figure 1:
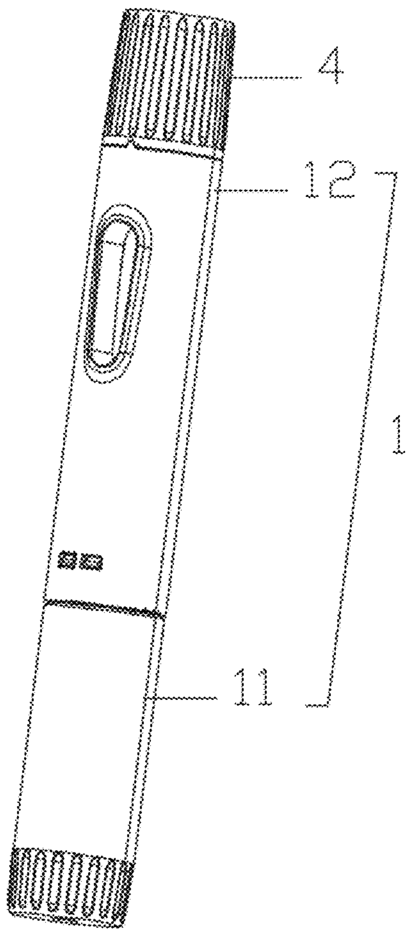
FIG. 1 is a perspective view of a disposable injection pen according to an embodiment of the present disclosure.

In the drawings: 1, pen casing; 11, upper casing portion; 12, lower casing portion; 2, injection head mechanism; 21, barrel; 22, needle; 23, rubber plug; 3, trigger mechanism; 31, protective sheath; 311, avoidance hole; 32, sliding part; 321, outer sliding block; 3211, guiding groove; 3212, guiding plate; 3213, blocking rib; 322, main body; 3221, cylinder; 3222, arc-shaped connecting plate; 3223, elastic hook A; 3224, arc-shaped insertion plate; 33, secondary spring; 34, push rod; 341, boss; 35, primary spring; 36, fixing block; 37, spring-guiding pin; 4, cap member; 41, cap head; 42, elastic hook B; and 43, needle cap.

DETAILED DESCRIPTION OF EMBODIMENTS

The technical solutions in the embodiments of the present application are provided to solve the above problems, and the general ideas are described as follows.

Embodiment 1

Referring to FIGS. 1-14, a disposable injection pen is provided, which includes a pen casing 1, an injection head mechanism 2 and a trigger mechanism 3.

The injection head mechanism 2 includes a barrel 21 arranged in the pen casing 1 and a needle 22 arranged on a top of the barrel 21. A rubber plug 23 is provided in the barrel 21.

Figure 3:
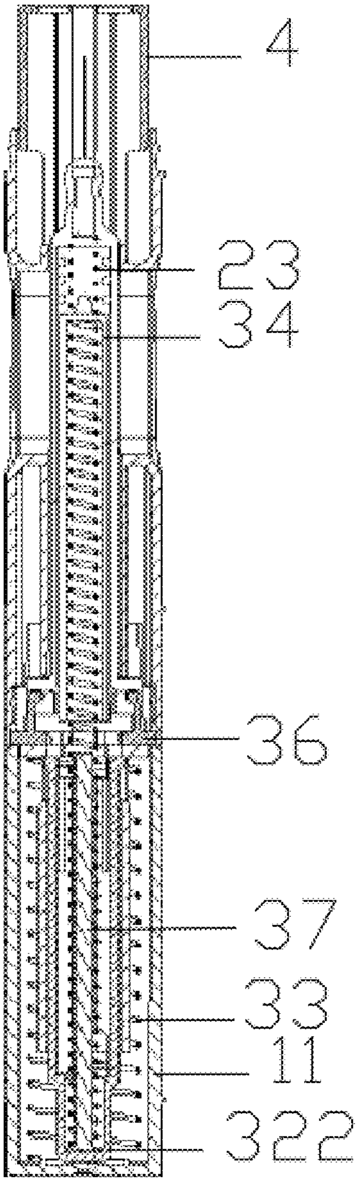
FIG. 3 is a section view of the disposable injection pen according to an embodiment of the present disclosure after completing an injection.
Figure 4:
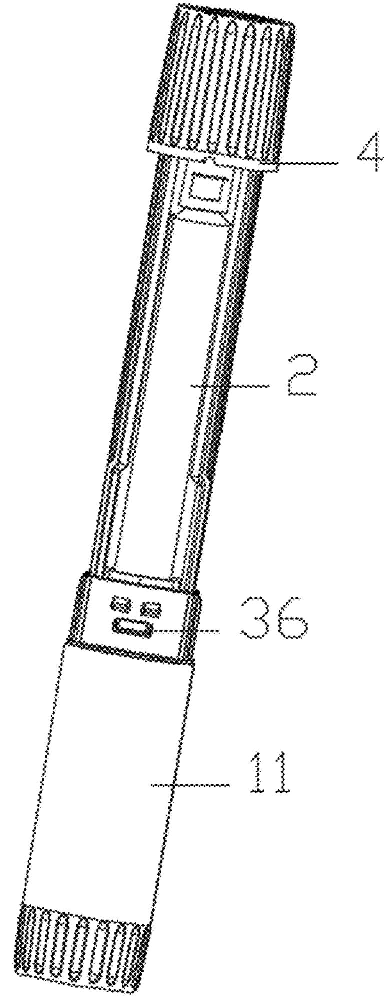
FIG. 4 is a schematic diagram of the disposable injection pen illustrated in FIG. 1 after removing a lower casing portion.

The trigger mechanism 3 includes a protective sheath 31 arranged in the pen casing 1, and the protective sheath is configured to movably wrap the needle 22. A bottom of the protective sheath 31 movably abuts against a sliding part 32. An outside of the sliding part 32 is sleeved with a secondary spring 33 whose bottom is fixedly connected to a bottom of the pen casing 1. A push rod with an open bottom is movably clamped inside the sliding part 32. An inner top of the push rod 34 is connected to an inner bottom of the sliding part 32 through a primary spring. When the injection pen is used for injection, as shown in FIG. 3, when the protective sheath 31 is pressed, the sliding part 32 moves downward such that the push rod 34 moves upward to push the rubber plug 23 forward. After the injection is completed, the push rod 34 is detached from an inner cavity of the sliding part 32, and the sliding part 32 is driven by the primary spring 35 to hit the bottom of the pen casing to produce a sound that indicates the completion of the injection. Specifically, the protective sheath 31 is pressed to drive an outer sliding block 321 to move downward to compress the secondary spring 33, rendering an arc-shaped connecting plate 3222 in the main body 322 to move downward. In this case, two bosses 341 on a side wall of a lower end of the push rod 34 will rotate along an inclined surface adherent to the arc-shaped connecting plate 3222 at a certain angle through a driving force of the primary spring to enter the inner cavity of the main body 322, such that the push rod 34 pushes the rubber plug 23 to inject the medicinal liquid. After the medicinal liquid injection is completed, the push rod 34 is detached from the inner cavity of the main body 322, and the main body 322 is driven by the primary spring 35 to hit the bottom of the upper casing portion 11 to produce a sound that indicates the completion of the injection.

Figure 2:
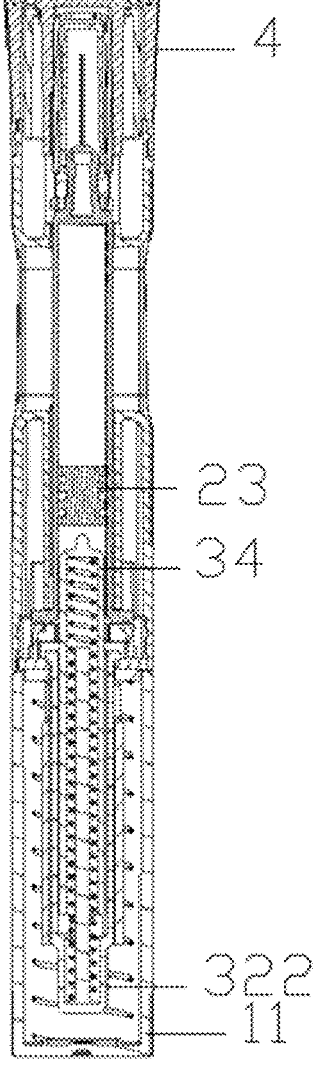
FIG. 2 is a section view of the disposable injection pen according to an embodiment of the present disclosure after assembled.

It should also be noted that the state of the trigger mechanism 3 before injection is shown in FIG. 2, where the bottom of the push rod 34 is clamped inside the sliding part 32.

Figure 5:
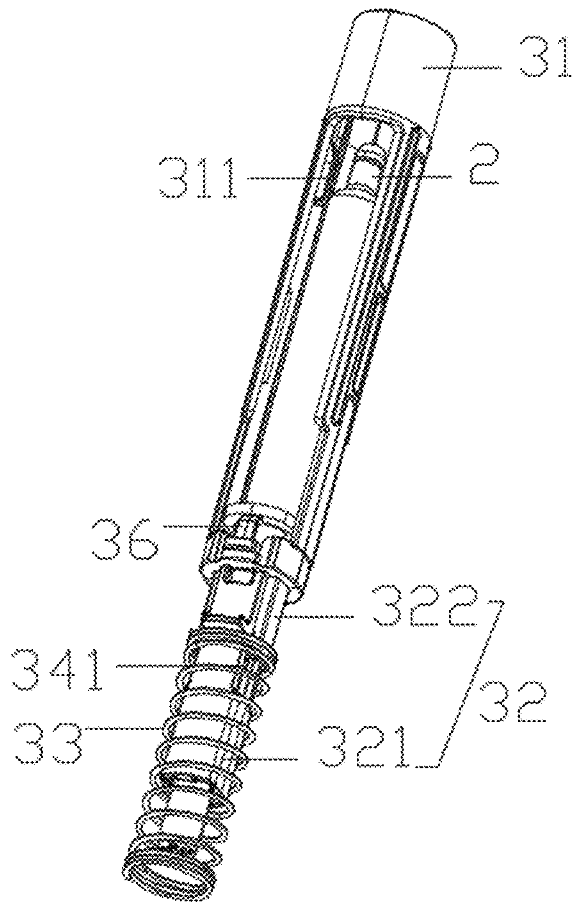
FIG. 5 schematically shows a connection relationship between a trigger mechanism and an injection head mechanism according to an embodiment of the present disclosure.
Figure 6:
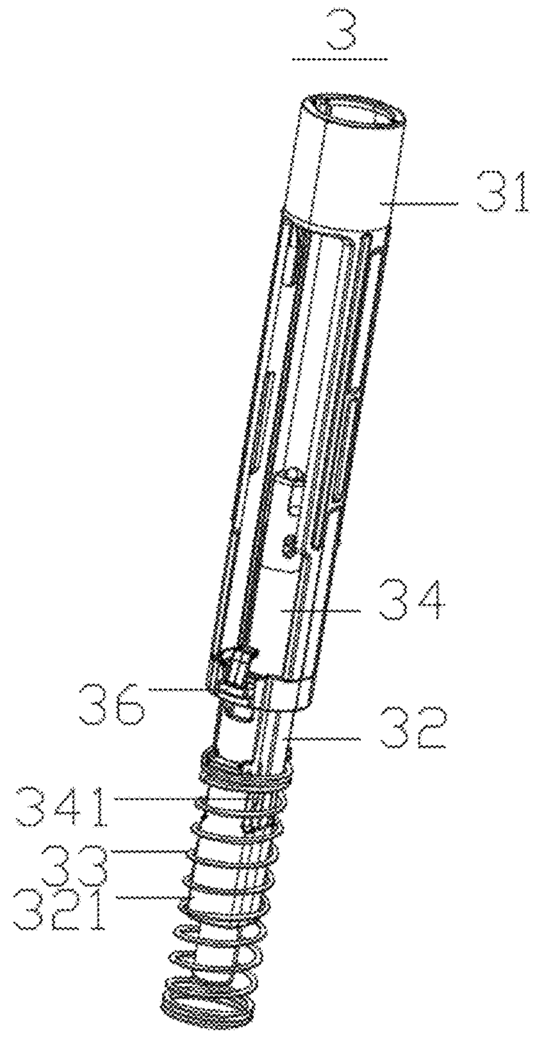
FIG. 6 is a schematic diagram of the trigger mechanism according to an embodiment of the present disclosure.

The pen casing 1 includes an upper casing portion 11 and a lower casing portion 12 fixedly clamped with each other. Two sides of an inner wall of the lower casing portion 12 are each provided with a protrusion (not shown in the drawings). The protrusion is fixed to the inner wall of the barrel 21. The lower casing portion 12 is fixed to the barrel 21 through the protrusion. Two sides of the protective sheath 31 are each provided with an avoidance hole fitting the protrusion. The avoidance hole 311 is illustrated in FIG. 5, which is configured to avoid the protrusion from interfering the downward movement of the protective sheath 31.

The sliding part 32 includes an outer sliding block 321 and a main body 322. Two sides of the outer sliding block 321 are each provided with a guiding groove 3211, and a guiding plate 3212 is fixed longitudinally in the guiding groove 3211. The main body 322 slides along the guiding plate 3212 to be sleeved into an inner cavity of the outer sliding block 321.

Two sides of an outer wall of the outer sliding block 321 are each provided with a blocking rib 3213. An upper end of the secondary spring 33 abuts against a lower of the blocking rib 3213, and the secondary spring 33 abuts against an inner bottom of the lower casing portion 12. By providing the blocking rib 3213, the secondary spring 33 can be compressed when the outer sliding block 321 moves downward.

The main body 322 of the sliding part 32 includes a cylinder 3221 and two arc-shaped connecting plates 3222 respectively connected to two sides of an upper portion of the cylinder 3221. An upper end of each of the two arc-shaped connecting plates 3222 is connected to an elastic hook A 3223 located at an opening of the upper end of the outer sliding block 321. A middle portion of each of the two arc-shaped connecting plates 3222 is connected with an arc-shaped insertion plate 3224, where the two arc-shaped insertion plates 3224 each have an opening opposite to each other, and each are fixed to a corresponding guiding plate 3212. The arc-shaped insertion plate 3224 and the guiding plate 3212 at the guide groove 3211 are operated such that the main body 322 can be fixedly connected to the outer sliding block 321. When the arc-shaped insertion plate 3224 slides to the lowest end of the guiding plate 3212, as shown in FIG. 3, the cylinder 3221 impacts with the bottom of the inner portion of the upper casing portion 11.

It should be noted that, in the unused state, the arc-shaped connecting plate 3222 is tightly pressed on the wall of the inner cavity of the outer sliding block 321. Under the impetus of the primary spring 35, the elastic hook A 3223 moves to the inner cavity of the outer sliding 321 and moves downward with the arc-shaped connecting plate 3222.

The push rod 34 is hollow, and two sides of an outer bottom of the push rod are each connected with a boss 341 located in the guiding groove 3211. The upper surface of the boss 341 inclinedly fits the side wall of the arc-shaped connecting plate 3222. When the arc-shaped connecting plate 3222 moves downward, the boss 341 is slidably inserted into a corresponding arc-shaped insertion plate 3224 and contacts with the guiding plate 3212. In this case, the primary spring 35 is twisted and loses the external force, so that the two bosses 341 are twisted at a certain angle by the primary spring 35 and thus move into the arc-shaped connecting plate 3222, so as to fit two L-shaped limiting arms on a fixing block 36 lately, thereby preventing the push rod 34 from continuing to move upward.

Figure 7:
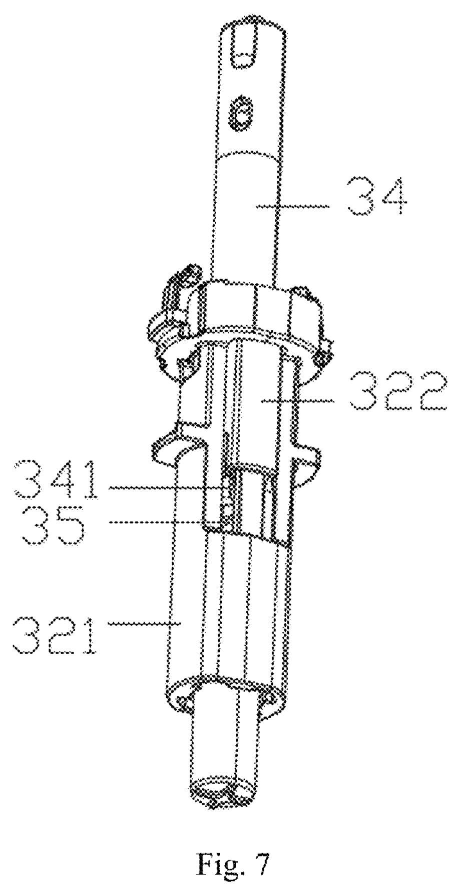
FIG. 7 schematically shows a connection relationship between a boss and a sliding part according to an embodiment of the present disclosure.
Figure 8:
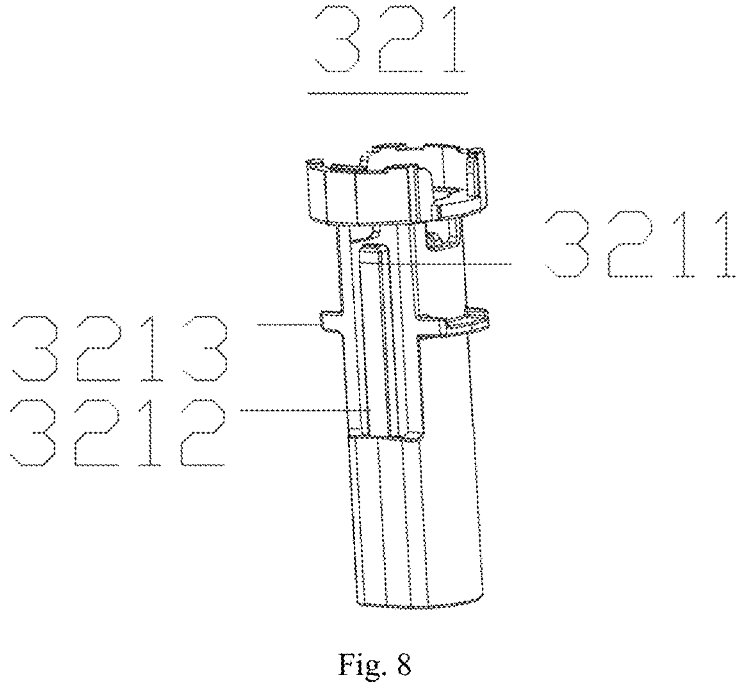
FIG. 8 is a schematic diagram of an outer sliding block according to an embodiment of the present disclosure.
Figure 9:
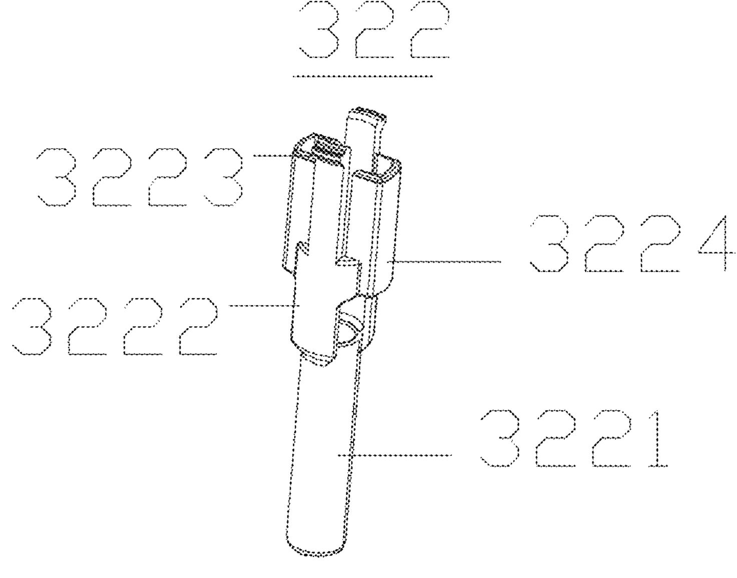
FIG. 9 is a schematic diagram of a main body of the sliding part according to an embodiment of the present disclosure.
Figure 10:
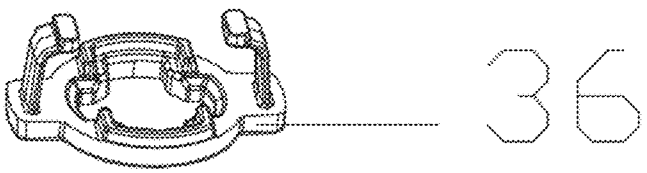
FIG. 10 is a schematic diagram of a fixing block according to an embodiment of the present disclosure.
Figure 11:
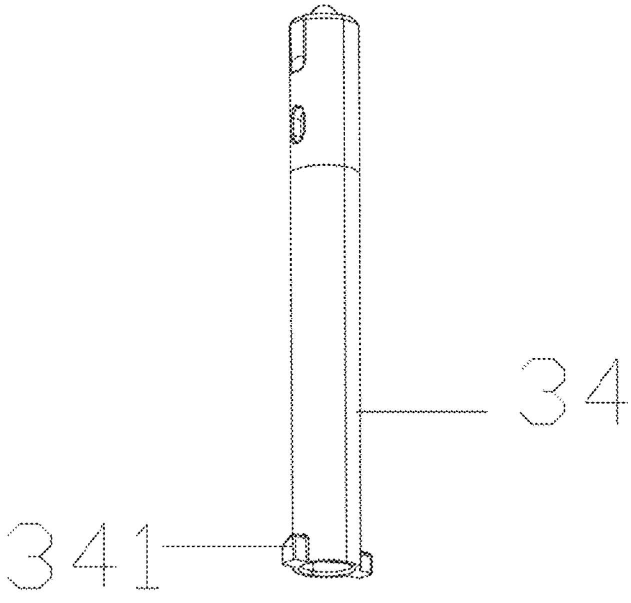
FIG. 11 is a schematic diagram of a push rod according to an embodiment of the present disclosure.
Figure 12:
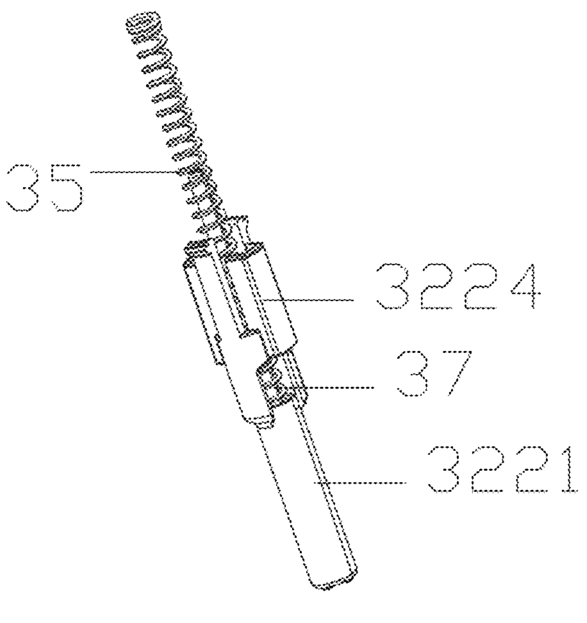
FIG. 12 schematically shows a connection relationship among a cylinder, a primary spring and a spring-guiding pin according to an embodiment of the present disclosure.
Figure 13:
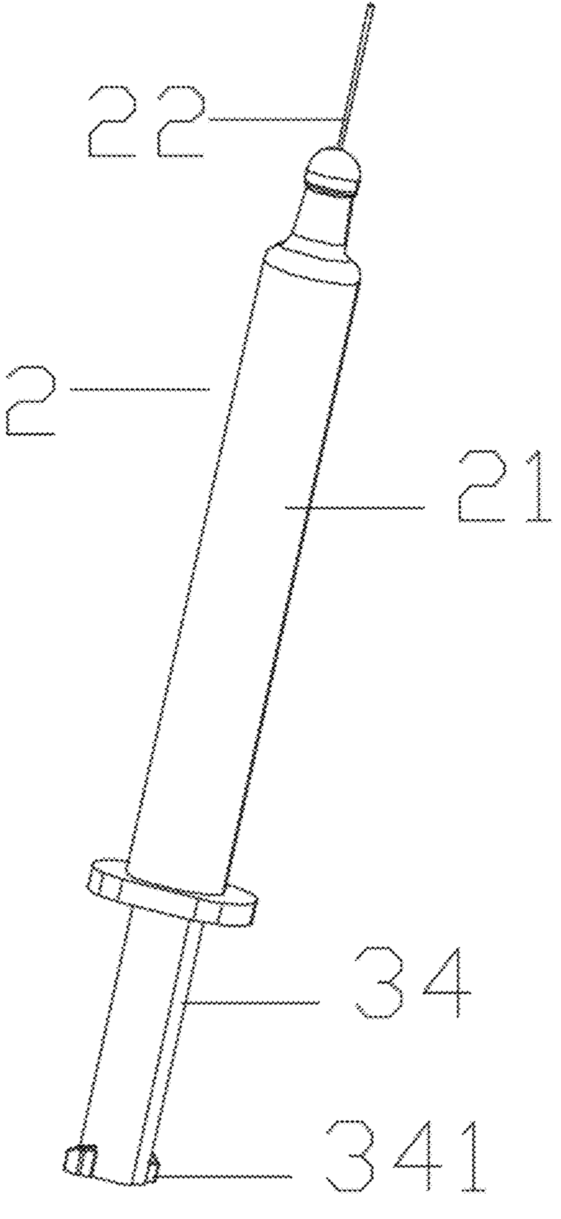
FIG. 13 schematically shows a connection relationship between the injection head mechanism and the push rod according to an embodiment of the present disclosure.

It should be noted that in the unused state, the two bosses 341 are stuck at the inclined surface of the arc-shaped connecting plate 3222, so that the position of the push rod 34 relative to the main body 322 is as shown in FIG. 7.

An opening of an upper end of the outer sliding block 321 is connected to a fixing block 36 in movable contact with the boss 341. An upper surface of the fixing block 36 is in movable contact with a lower surface of the elastic hook A 3223. Each of two outer walls of the fixing block 36 has a protruding portion. Two side of an inner wall of the lower casing portion 12 are each provided with a clamping slot fitting the protruding portion.

The primary spring 35 is fixedly connected between an inner bottom of the cylinder 3221 and an inner top of the push rod 34. The primary spring 35 is configured to push the push rod 34 to move upward and against the rubber plug 23, thereby facilitating the medicament injection.

It should be noted that while the push rod 34 moves into the inner cavity of the main body 322, the primary spring 35 extends, thereby pushing the push rod 34 upward and the main body 322 downward along the guiding groove 3211. When the medicament injection is completed, as shown in FIG. 3, the push rod 34 pushes the rubber stopper 23 against the inner cavity of the barrel 21 near the needle 22, so that the main body 322 strikes the bottom of the upper casing portion 11 to produce an end sound indicating the completion of the medicament injection.

A spring-guiding pin 37 is fixedly connected to the bottom of the inside of the cylinder 3221, and the primary spring 35 is wound around the outside of the spring-guiding pin 37. The spring-guiding pin 37 has a guiding effect on the movement of the primary spring 35, thereby reducing the bending of the primary spring 35 during the movement.

Figure 14:
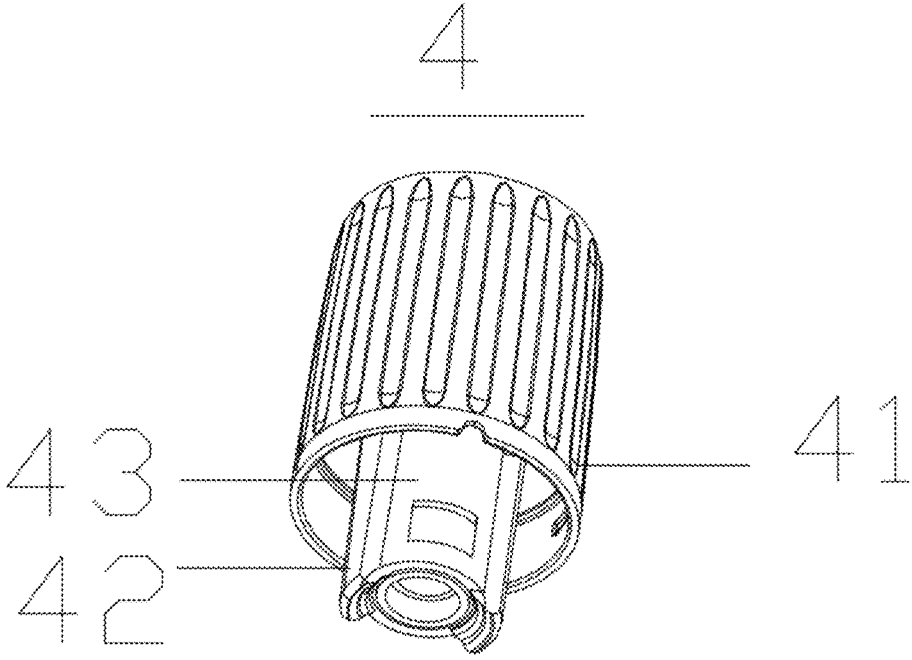
FIG. 14 shows a schematic diagram of a cap member according to an embodiment of the present disclosure.

The upper end of the lower casing portion 12 is in snap-fit connection with a cap member 4. The cap member 4 includes a cap head 41, an elastic hook B 42 and a needle cap 43. As shown in FIG. 14, the elastic hook B 42 is connected to two sides of the inner top of the cap head 41, and the needle cap 43 is in snap-fit connection with the cap head 41 through the elastic hook B 42, and is configured to movably cover a periphery of the needle head 22 through the elastic hook B 42, thereby allowing the needle cap 43 to be arranged on the periphery of the needle head 22.

The method of using the disposable injection pen provided herein is described below, which includes the following steps.

(S1) The pen cap member 4 and two elastic hooks B 42 connected to the cap head 41 are removed to pull out the needle cap 43.

(S2a) The protective sheath 31 is pressed to drive the outer sliding block 321 to move downward and compress the secondary spring 33, and then the arc-shaped connecting plate 3222 in the main body 322 will also move downward. In this case, the two bosses 341 on the side wall at the lower end of the push rod 34 will rotate at a certain angle along the inclined surface that fits with the arc-shaped connecting plate 3222 into the inner cavity of the main body 322 through the push force of the main spring 35, and the push rod 34 pushes the rubber plug 23 to inject the medicinal liquid.

(S2b) When the medicinal liquid injection is completed, the push rod 34 disengages from the inner cavity of the main body 322, and the main body 322 is bounced to the bottom of the upper casing portion 11 by the primary spring 35 and subjected to impact to produce an end sound indicating the completion of the medicinal liquid injection.

(S3) After the medicinal liquid injection is completed, the injection pen is removed. At this time, the pre-compressed secondary spring 33 pushes the outer sliding block 321 and the protective sheath 31 to move forward. When the outer sliding block 321 returns to the original position, the two elastic hooks A 3223 at the upper end of the main body 322 are respectively clamped into the two square holes in the side wall at the upper end of the outer sliding block 321. The protective sheath 31 is pressed again, and the protective case 31 is prevented from moving due to the support of the elastic hooks A 3223 of the main body 322 for the outer sliding block 321, forming an anti-needling function.

In addition, the disposable injection pen provided herein has the following beneficial effects.

(1) The disposable injection pen has high efficiencies.

(2) The disposable injection pen has reduced precision requirements. Specifically, compared with the traditional limiting form using hold folder and the push rod, the unique trigger mechanism 3 used herein has lower accuracy requirements for size of products. The accuracy requirements for part in the traditional structure +/−0.05 mm, while +/−0.1 mm in this application. In this case, the production yield and efficiency can be improved, and the reliability is also more stable compared with the traditional structures after being tested and verified.

(3) The disposable injection pen provided herein requires less parts. Specifically, the number of parts of the traditional injection pen in 13-18, while the number of parts of the disposable injection pen in this application in 11. Due to the structural advantages, the number of parts can be significantly reduced.

(4) The injection moulding cycle of plastic parts is reduced. Specifically, for the traditional injection pen, the injection moulding cycle of all plastic parts is 190-210 s, while the injection moulding cycle of plastic parts in the present application is 145-165 s. Thus, the injection moulding time is reduced, leading to increased efficiency.

(5) Fewer automatic equipment stations are required in the present disclosure. Specifically, as the number of parts is reduced, the number of supporting automatic chemical stations is also reduced accordingly, which can save resources.

(6) Automated assembly cycle is shortened. The disposable injection pen has simple structures and few parts, and is easy to assemble. The current assembling efficiency of the disposable injection pen in this application is 15-17 s/pcs, while 18-20 s/pcs in the traditional injection pen. In this regard, this application has significant advantages compared with the prior arts.

(7) The disposable injection pen provided herein has a superior stability. To be specific, the core components are set up such that the locking structure of the push rod 34 is unique. After dropping, vibration and other tests, no false triggering phenomenon occurs, indicating that the performance of the disposable injection penis very reliable.

(8) The protective sheath 31 in this application has repeated protective function. Specifically, the current protective sheath in this application can withstand a force more than 150 N. When the applied force is greater than 150 N and the protective function fails, the protective sheath can still offer the protective effect after the applied force is released.

(9) The disposable injection pen provided herein can be recycled and reused. To be specific, some parts of the disposable injection pen can be recycled and reused, such as the pen cap member 4, the pen casing 2, and the secondary spring 33, which can save social resources.

Finally, it should be noted that described above are merely examples for the purpose of clearly illustrating the present disclosure, and are not intended to limit the disclosure. Though the disclosure has been described in detail above, various variations or changes can still be made by one of ordinary skill in the art to the embodiments disclosed herein. It should be noted that those made without departing from the spirit of the disclosure shall still fall within the scope of the present disclosure defined by the appended claims.

What is claimed is:

1. A disposable injection pen, comprising:

a pen casing;

an injection head mechanism; and a trigger mechanism;

wherein the injection head mechanism comprises a barrel arranged in the pen casing and a needle arranged on a top of the barrel; and a rubber plug is provided in the barrel; and the trigger mechanism comprises a protective sheath arranged in the pen casing, and the protective sheath is configured to movably wrap the needle; a bottom of the protective sheath movably abuts against a sliding part; an outside of the sliding part is sleeved with a secondary spring whose bottom is fixedly connected to a bottom of the pen casing; a push rod with an open bottom is movably clamped inside the sliding part; an inner top of the push rod is connected to an inner bottom of the sliding part through a primary spring; when the protective sheath is pressed, the sliding part moves downward such that the push rod moves upward to push the rubber plug forward; and after an injection is completed, the push rod is detached from an inner cavity of the sliding part, and the sliding part is driven by the primary spring to hit the bottom of the pen casing to produce a sound that indicates completion of the injection wherein the pen casing comprises an upper casing portion and a lower casing portion fixedly clamped with each other; two sides of an inner wall of the lower casing portion are each provided with a protrusion; the protrusion is fixed to an inner wall of the barrel; and two sides of the protective sheath are each provided with an avoidance hole fitting the protrusion;

wherein the sliding part comprises an outer sliding block and a main body; two sides of the outer sliding block are each provided with a guiding groove, and a guiding plate is fixed longitudinally in the guiding groove; and the main body of the sliding part is configured to slide along the guiding plate to be sleeved into an inner cavity of the outer sliding block.

2. The disposable injection pen of claim 1, wherein two sides of an outer wall of the outer sliding block are each provided with a blocking rib; an upper end of the secondary spring abuts against a lower side of the blocking rib; and the secondary spring abuts against an inner bottom of the lower casing portion.

3. The disposable injection pen of claim 2, wherein the main body of the sliding part comprises a cylinder and two arc-shaped connecting plates respectively connected to two sides of an upper portion of the cylinder; an upper end of each of the two arc-shaped connecting plates is connected to a first elastic hook located at an opening of an upper end of the outer sliding block; and a middle portion of each of the two arc-shaped connecting plates is connected with an arc-shaped insertion plate, wherein two arc-shaped insertion plates each have an opening opposite to each other, and each are fixed to a corresponding guiding plate.

4. The disposable injection pen of claim 3, wherein the push rod is hollow; two sides of an outer bottom of the push rod are each connected with a boss located in the guiding groove; an upper surface of the boss is configured to inclinedly fit a side wall of the arc-shaped connecting plate; and the boss is configured to be slidably inserted into a corresponding arc-shaped insertion plate and to be in contact with the guiding plate during a downward movement of the arc-shaped connecting plate.

5. The disposable injection pen of claim 4, wherein the opening of the upper end of the outer sliding block is connected to a fixing block in movable contact with the boss; an upper surface of the fixing block is in movable contact with a lower surface of the first elastic hook; each of two outer walls of the fixing block has a protruding portion; and two sides of an inner wall of the lower casing portion are each provided with a clamping slot fitting the protruding portion.

6. The disposable injection pen of claim 5, wherein the primary spring is fixedly connected between an inner bottom of the cylinder and an inner top of the push rod.

7. The disposable injection pen of claim 6, wherein a spring-guiding pin is fixedly connected to the inner bottom of the cylinder; and the primary spring is wound around an outside of the spring-guiding pin.

8. The disposable injection pen of claim 7, wherein an upper end of the lower casing portion is in snap-fit connection with a cap member; the cap member comprises a cap head, a second elastic hook and a needle cap; the second elastic hook is connected to two sides of an inner top of the cap head; and the needle cap is in snap-fit connection with the cap head through the second elastic hook, and is configured to movably cover a periphery of the needle.

* * * * *